(12) United States Patent
Harrup et al.

(10) Patent No.: US 8,592,628 B2
(45) Date of Patent: Nov. 26, 2013

(54) PHOSPHAZENE ADDITIVES

(75) Inventors: Mason K. Harrup, Idaho Falls, ID (US); Harry W. Rollins, Idaho Falls, ID (US)

(73) Assignee: Battelle Energy Alliance, LLC, Idaho Falls, ID (US)

( * ) Notice: Subject to any disclaimer, the term of this patent is extended or adjusted under 35 U.S.C. 154(b) by 120 days.

(21) Appl. No.: 13/117,579

(22) Filed: May 27, 2011

(65) Prior Publication Data
US 2011/0301286 A1    Dec. 8, 2011

Related U.S. Application Data

(60) Provisional application No. 61/351,110, filed on Jun. 3, 2010.

(51) Int. Cl.
C07F 9/547    (2006.01)
(52) U.S. Cl.
USPC .................................. 564/13; 564/14; 524/13
(58) Field of Classification Search
USPC .......................... 508/422; 564/13, 14; 524/13
See application file for complete search history.

(56) References Cited

U.S. PATENT DOCUMENTS

| | | | |
|---|---|---|---|
| 3,711,542 A | 1/1973 | Hook et al. | |
| 4,042,561 A | 8/1977 | DeEdwardo et al. | |
| 4,079,035 A | 3/1978 | Brackenridge | |
| 4,107,108 A | 8/1978 | Dieck et al. | |
| 4,108,805 A | 8/1978 | Dieck et al. | |
| 4,440,921 A | 4/1984 | Allcock et al. | |
| 4,535,147 A | 8/1985 | Myers | |
| 4,988,791 A | 1/1991 | Maruyama et al. | |
| 5,250,626 A | 10/1993 | Landry et al. | |
| 5,830,600 A * | 11/1998 | Narang et al. | 429/326 |
| 5,834,020 A | 11/1998 | Margerum et al. | |
| 6,544,690 B1 | 4/2003 | Harrup et al. | |
| 6,596,893 B2 | 7/2003 | Nakacho et al. | |
| 6,713,168 B2 | 3/2004 | Liu et al. | |
| 6,797,750 B2 | 9/2004 | Taniguchi et al. | |
| 7,008,564 B2 | 3/2006 | Harrup et al. | |
| 7,285,362 B2 | 10/2007 | Harrup et al. | |

(Continued)

FOREIGN PATENT DOCUMENTS

CN    101698701 A  *  4/2010

OTHER PUBLICATIONS

Dell, D., et al., "Phosphorus-Nitrogen Compounds. Part XIII. Phenoxy and p-Bromophenoxy-chlorocyclotriphosphazatrienes," J. Chem. Soc., 1965, 4070-4073.*

(Continued)

*Primary Examiner* — Liam Heincer
*Assistant Examiner* — Nicholas Hill
(74) *Attorney, Agent, or Firm* — TraskBritt (57) ABSTRACT

An additive comprising a phosphazene compound that has at least two reactive functional groups and at least one capping functional group bonded to phosphorus atoms of the phosphazene compound. One of the at least two reactive functional groups is configured to react with cellulose and the other of the at least two reactive functional groups is configured to react with a resin, such as an amine resin or a polycarboxylic acid resin. The at least one capping functional group is selected from the group consisting of a short chain ether group, an alkoxy group, and an aryloxy group. Also disclosed are an additive-resin admixture, a method of treating a wood product, and a wood product.

8 Claims, 5 Drawing Sheets

(56) References Cited

U.S. PATENT DOCUMENTS

| | | |
|---|---|---|
| 2004/0138351 A1 | 7/2004 | Kaprinidis et al. |
| 2005/0245656 A1 | 11/2005 | Sinclair |
| 2005/0272838 A1 | 12/2005 | Yang et al. |
| 2008/0051495 A1 | 2/2008 | Murakami et al. |

OTHER PUBLICATIONS

Chen-Yang, Y. W., et al., "Preparation and Characterization of (Aryloxy)chlorocyclotriphosphazenes by Phase Transfer Catalysis," Polyhedron, 1993, 12, 59-68.*

Bartsch, R. A., et al., "Structure-alkalai metal cation complexation relationships for macrocyclic PNP-lariat ether ligands," J. Chem. Soc., Perkin Trans. 2, 2002, 442-448.*

Machine translation of CN101698701A. Performed via the Global Patent Search Network on USPTO website on Aug. 5, 2013.*

Improving Fire Performance of Wood, http://virtual.vtt.fi/virtual/innofirewood/stateoftheart/database/improving/improving.html, 14 pages, accessed Sep. 17, 2007.

PCT International Search Report and Written Opinion of the International Searching Authority for PCT/US11/38748, dated Nov. 15, 2011, 8 pages.

* cited by examiner

PHOSPHAZENE ADDITIVES

CROSS-REFERENCE TO RELATED APPLICATION

This application claims the benefit of U.S. Provisional Patent Application Ser. No. 61/351,110, filed Jun. 3, 2010, the disclosure of which is hereby incorporated herein in its entirety by this reference.

STATEMENT REGARDING FEDERALLY SPONSORED RESEARCH OR DEVELOPMENT

This invention was made with government support under Contract Number DE-AC07-051D14517 awarded by the United States Department of Energy. The government has certain rights in the invention.

TECHNICAL FIELD

The present invention, in various embodiments, relates generally to additives for use in wood products, wood products impregnated with the additives, and methods of treating wood products to improve their mechanical strength, flame retardance, and water resistance.

BACKGROUND

Wood is a highly flammable material used in many forms and configurations in construction of residential, commercial, and industrial structures. To decrease the flammability of products made from wood, fire retardants have been incorporated into the wood. For instance, polymer resins have been impregnated into the wood to improve its flame retardance and also to improve the strength, hardness, coloring, and useful lifetime of the wood. Such polymer resins include melamine-formaldehyde resins, urea-formaldehyde resins, and melamine-urea-formaldehyde resins.

Urea-formaldehyde resins are known in the art to be inexpensive and provide good thermal properties, excellent hardness, and an absence of color change to the treated wood. However, once cured, the urea-formaldehyde resins are susceptible to acid hydrolysis upon contact with water, resulting in the release of formaldehyde, which is toxic. To increase the durability of the wood, making it less likely to hydrolyze, melamine (1,3,5-triazine-2,4,6-triamine)-formaldehyde resins have been used. While melamine-formaldehyde resins are more heat resistant, less susceptible to acid hydrolysis, and more water resistant than urea-formaldehyde resins, the melamine-formaldehyde resins are more expensive to manufacture. Melamine-urea-formaldehyde resins have the desirable properties of urea-formaldehyde resins and melamine-formaldehyde resins: the cost-effective, urea-formaldehyde component and the hydrophobic, durable properties of the melamine-formaldehyde component. When compared to a urea-formaldehyde resin, a melamine-urea-formaldehyde resin is more durable and hydrophobic and emits less formaldehyde.

Phosphazene compounds have been used to improve the flame retardance of polymeric substrates, such as wood or textiles. The phosphazene compound is mixed or blended with the polymeric substrate. Phosphazene compounds have also been reacted with the polymeric substrate to improve its flame retardance. For instance, N-methylol phosphazene compounds have been reacted with cellulosic materials or polymers to provide flame retardance.

BRIEF SUMMARY

In one embodiment, an additive comprising at least two reactive functional groups and at least one capping functional group bonded to phosphorus atoms of a first phosphazene compound is disclosed. One of the at least two reactive functional groups is configured to react with cellulose and the other of the at least two reactive functional groups is configured to react with a resin. The at least one capping functional group is selected from the group consisting of a short chain ether group, an alkoxy group, and an aryloxy group.

In another embodiment, an additive-resin admixture comprising an additive admixed with a resin is also disclosed. The additive comprises a phosphazene compound comprising at least two reactive functional groups and at least one capping functional group bonded to phosphorus atoms of the phosphazene compound. One of the reactive functional groups is configured to react with cellulose and the other reactive functional group is configured to react with the resin. The at least one capping functional group is selected from the group consisting of a short chain ether group, an alkoxy group, and an aryloxy group.

In a further embodiment, a method of treating a wood product is also disclosed. The method comprises mixing an additive with a resin to form an additive-resin admixture and impregnating the additive-resin admixture into a wood product. The additive comprises at least two reactive functional groups and at least one capping functional group bonded to phosphorus atoms of a phosphazene compound. The at least two reactive functional groups are configured to react with at least one of cellulose and the resin, and the at least one capping functional group is selected from the group consisting of a short chain ether group, an alkoxy group, and an aryloxy group.

In yet another embodiment, a wood product is also disclosed. A phosphazene compound is bonded to cellulose of a wood product through a first phosphorus atom of the phosphazene compound and to a resin through a second phosphorus atom of the phosphazene compound. The phosphazene compound comprises at least one capping functional group bonded to at least one phosphorus atom of the phosphazene compound. The at least one capping functional group is selected from the group consisting of a short chain ether group, an alkoxy group, and an aryloxy group.

DETAILED DESCRIPTION

An additive for use in providing flame retardance and mechanical stability to a wood product is disclosed. As used herein, the term "wood" means and includes a flammable material formed from cellulose or hemicellulose fibers bonded together by lignin. The term "wood product" means and includes lumber or a composite material that includes wood and at least one other material, such as at least one of an adhesive, binder, resin, and wax. The wood product may be particle board, fiber board, oriented strand board, wafer board, chip board, plywood, agricultural straw board, saw dust, or wood chips. The additive is a phosphazene compound having at least two functional groups. One of the functional groups is configured to react with cellulose in the wood product while the other functional group is configured to react with a resin impregnated in the wood product. These functional groups are collectively referred to herein as reactive functional groups (RFGs). The resin may be a polymer resin, such as an amine resin or a polycarboxylic acid (PCA) resin. The additive also includes at least one capping functional group (CFG). In addition to being substantially non-reactive, the capping functional group is configured to tailor the solubility and hydrophobicity of the additive such that the additive is miscible in a formulation of the resin. The additive may, optionally, include a second phosphazene compound having one reactive functional group and at least one capping functional group. The reactive functional group of the second phosphazene compound may be configured to react with the resin or with additional molecules of the first phosphazene compound. The additive may provide flame retardance to the wood product and be condensable with functional groups on the resin and on the wood product. The additive may be incorporated into the wood product, such as 2×6 boards or 4×4 boards, which are used in outdoor decking materials.

While the molecular weight of the additive is not limited, the additive may have a minimum molecular size such that a reaction product of the additive and the resin penetrates fibers of the wood product. To achieve the desired molecular size, the reactive functional groups and the capping functional groups may be selected to contribute a minimum molecular size to the total molecular size of the additive while still providing flame retardance and the desired solubility and hydrophobicity properties to the wood product.

The phosphazene compound includes a plurality of phosphorous-nitrogen units with the reactive functional groups and the capping functional groups bonded to phosphorus atoms of the phosphorous-nitrogen units. Each phosphorous-nitrogen unit includes a double bond between the phosphorus atom and the nitrogen atom and each phosphorous-nitrogen unit is bonded to an adjacent phosphorous-nitrogen unit through a single bond. The phosphazene compound has the general structure shown below:

where n is an integer from 1 to 10 and X is a reactive functional group or a capping functional group. By way of non-limiting example, n may be an integer between 2 and 9 or between 3 and 8. The phosphazene compound may be cyclic or linear. In one embodiment, the phosphazene compound includes three phosphorous-nitrogen units (n=3). In another embodiment, the phosphazene is cyclic. A general structure for an additive where n=3 is shown below:

where CFG refers to a capping functional group and RFG refers to a reactive functional group. While various embodiments herein describe or illustrate the phosphazene compound as a six-membered cyclic compound, i.e., n=3, the phosphazene compound may be from a six-membered to a sixteen-membered cyclic compound.

The functional group utilized as the capping functional group may affect at least one of the miscibility and hydrophobicity of the additive in the resin formulation, which is typically an aqueous-based solvent mixture. A single capping functional group may provide the desired miscibility and hydrophobicity to the additive or multiple, different capping functional groups may be used to provide the desired miscibility and hydrophobicity. By utilizing capping functional groups that are less hydrophobic, the additive may be more soluble or miscible in the resin formulation. Conversely, by utilizing capping functional groups that are more hydrophobic, the additive may be less miscible in the resin formulation. The capping functional group may include at least one heteroatom including, but not limited to, oxygen, nitrogen, sulfur, selenium, or tellurium. If, however, the capping functional group is bonded to the phosphorus atom of the phosphazene compound through the heteroatom, the heteroatom may be oxygen, sulfur, selenium, or tellurium. While nitrogen may be present in the capping functional group, the capping functional group may not be bonded to the phosphorus atom of the phosphazene compound through the nitrogen atom.

Capping functional groups that provide solubility of the additive in the resin formulation are referred to herein as "solubility imparting functional groups." Capping functional groups that provide hydrophobicity to the additive in the resin formulation are referred to herein as "hydrophobicity imparting functional groups." The presence of solubility imparting functional groups on the phosphazene compound may improve the solubility of the additive in the resin formulation, while the presence of hydrophobicity imparting functional groups may provide increased water resistance and decreased flammability (increased flame retardance) to the wood product impregnated with the additive. By balancing the number of solubility imparting functional groups and hydrophobicity imparting functional groups on the additive, the desired balance of solubility, water resistance, and flame retardance may be achieved. To provide optimized solubility and increased flame retardance, the additive may include a minimum number of solubility imparting functional groups and a maximum number of hydrophobicity imparting functional groups.

The solubility imparting functional group includes, but is not limited to, a short chain ether group, an alkoxy group, an amine group, or a thioether group. If the solubility imparting functional group is the short chain ether group or the alkoxy group, the capping functional group may be bonded to the phosphorus atom of the phosphazene compound through the oxygen atom. The short chain ether group may have the following structure:

where R is a methyl, ethyl, propyl, or butyl group. A precursor or reagent for the short chain ether group may be a primary alcohol that includes the short chain ether group. The alkoxy group may include an alkyl group having between one carbon atom and four carbon atoms bonded to the oxygen atom. A precursor or reagent for the alkoxy group may be a linear or branched primary alcohol having between one carbon atom and four carbon atoms. A precursor or reagent for the amine group may be a linear or branched secondary amine having between one carbon atom and four carbon atoms. A precursor or reagent for the thioether group may be a linear or branched primary thiol having between one carbon atom and four carbon atoms.

The hydrophobicity imparting functional group may be an aromatic group bonded to the phosphazene compound through an oxygen atom, such as an aryloxy group. The aryl group may include from six carbon atoms to twenty carbon atoms. The aryl group may include, but is not limited to, aceanthrylene, acenaphthylene, acephenanthrylene, anthracene, azulene, benzene, chrysene, coronene, fluoranthene, fluorene, hexacene, hexaphene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, or trinaphthalene. The aryloxy group may include additional substituents or may be unsubstituted. The substituents may be in the ortho, meta, or para positions relative to the oxygen atom of the aryloxy group. If substituted, the substituent may include, but is not limited to, an alkyl group or halogen group. The hydrophobicity imparting functional group may include, but is not limited to, a mono-, di-, or tri-substituted phenoxy group. The hydrophobicity imparting functional group may also include a hydrocarbon spacer between the oxygen atom and the aromatic group, such as a methylene group or ethylene group. By way of non-limiting example, the hydrophobicity imparting functional group may be a halogenated phenoxy group, such as a brominated phenoxy group. However, halogens other than bromine may be used.

The first phosphazene compound of the additive may include at least two reactive functional groups, one reactive functional group configured to react with hydroxyl groups of the cellulose and the other reactive functional group configured to react with amine functional groups or polycarboxylic acid functional groups on the resin. If the resin is an amine resin, one of the reactive functional groups of the first phosphazene compound may be configured to react with amine groups on the resin. If the resin is a PCA resin, one of the reactive functional groups may be configured to react with carboxylic acid groups on the resin. A condensation reaction may occur between one of the reactive functional groups on the first phosphazene compound and the resin, cross-linking the first phosphazene compound and the resin. A condensation reaction may also occur between the other reactive functional group on the first phosphazene compound and the hydroxyl groups on the cellulose, cross-linking the first phosphazene compound and the wood. By way of non-limiting example, the reactive functional group on the first phosphazene compound may be a halogen atom, such as fluorine, chlorine, bromine, iodine, or combinations thereof. The reactive functional group may be selected so as to be sufficiently reactive to form desired bonds with the resin. However, the reactive functional group may also be sufficiently stable so as not to substantially react with the resin before or during the wood impregnation process, ensuring that the first phosphazene compound remains of minimum molecular size to facilitate its penetration into the wood product.

By way of non-limiting example, the capping functional groups on the first phosphazene compound may include short chain ether groups (as the solubility imparting functional groups) and a halogenated phenolic group (as the hydrophobicity imparting functional group). In one embodiment, the first phosphazene compound of the additive has the structure below:

where the methoxyethoxy groups and the brominated phenoxy group are the capping functional groups and the chlorine atoms are the reactive functional groups. While the illustrated additive includes three methoxyethoxy groups, one brominated phenoxy group, and two chlorine groups, phosphazene compounds having other combinations of these functional groups may be produced and used as the additive. In addition, additives having other functional groups, as described above, may be produced, depending on the desired properties of the additive.

To form the additive, a phosphazene starting material may be reacted with at least one reagent that functions as a precursor of the capping functional group. By way of non-limiting example, to form the additive illustrated above, hexachlorocyclotriphosphazene ($N_3P_3Cl_6$) may be used as the phosphazene starting material. $N_3P_3Cl_6$ is commercially available, such as from Sigma-Aldrich Co. (St. Louis, Mo.). While specific embodiments herein describe using $N_3P_3Cl_6$ as the phosphazene starting material to form a specific additive, additional phosphazene starting materials may be used, depending on the specific additive to be formed. By way of non-limiting example, octachlorocyclotetraphosphazene ($N_4P_4Cl_8$), which is also commercially available, may be used as the phosphazene starting material if the additive is to include four phosphorus-nitrogen units. For ease of synthesis, the phosphazene starting material may include chlorine atoms or other halogen atoms that function as the reactive functional groups. For instance, at least two of the chlorine atoms of the $N_3P_3Cl_6$ may remain and may function as the reactive functional groups of the first phosphazene compound of the additive that is ultimately formed. One of the chlorine atoms of the $N_3P_3Cl_6$ may remain and may function as the reactive functional groups of the second phosphazene compound of the additive that is ultimately formed. However, if the phosphazene starting material does not include functional groups capable of functioning as the reactive functional groups, the reactive functional groups may be incorporated into the phosphazene starting material by conventional techniques, which are not described in detail herein.

The reagents that function as precursors of the capping functional groups may be nucleophilic compounds that react with the phosphorus atoms of the $N_3P_3Cl_6$, replacing a portion of the chlorine atoms with the capping functional groups. The reagents may be selected depending on the capping functional groups to be present on the additive. By way of non-limiting example, if the additive illustrated above is to be formed, reagents that function as precursors of the capping functional groups may be 4-bromophenol and 2-methoxyethanol, which are commercially available, such as from Sigma-Aldrich Co. (St. Louis, Mo.).

The solubility of the additive in the resin formulation may be affected by the ratio of solubility imparting functional groups to hydrophobicity imparting functional groups on the additive. An additive with an increased number of solubility imparting functional groups relative to hydrophobicity imparting functional groups may have increased solubility in the resin formulation. Conversely, an additive with an increased number of hydrophobicity imparting functional groups relative to solubility imparting functional groups may have increased flame retardance. Therefore, to maximize the flame retardant properties of the additive, the minimum number of solubility imparting functional groups may be present on the additive to provide the desired solubility in the resin formulation. By controlling the ratio or stoichiometry of the reagents and the phosphazene starting material, the additive having the desired functional groups may be formed. By way of non-limiting example, if the additive is a six-membered cyclic compound, i.e., n=3, the number of solubility imparting functional groups on the phosphazene compound may be from 0 to 6, the number of hydrophobicity imparting functional groups may be from 0 to 6, and the number of reactive functional groups may be from 1 to 6. In one embodiment, the reaction conditions are controlled such that two chlorine atoms are present on the additive, which enables the additive to react with the wood product and the resin. The four remaining substituents are capping functional groups.

Figure 1:
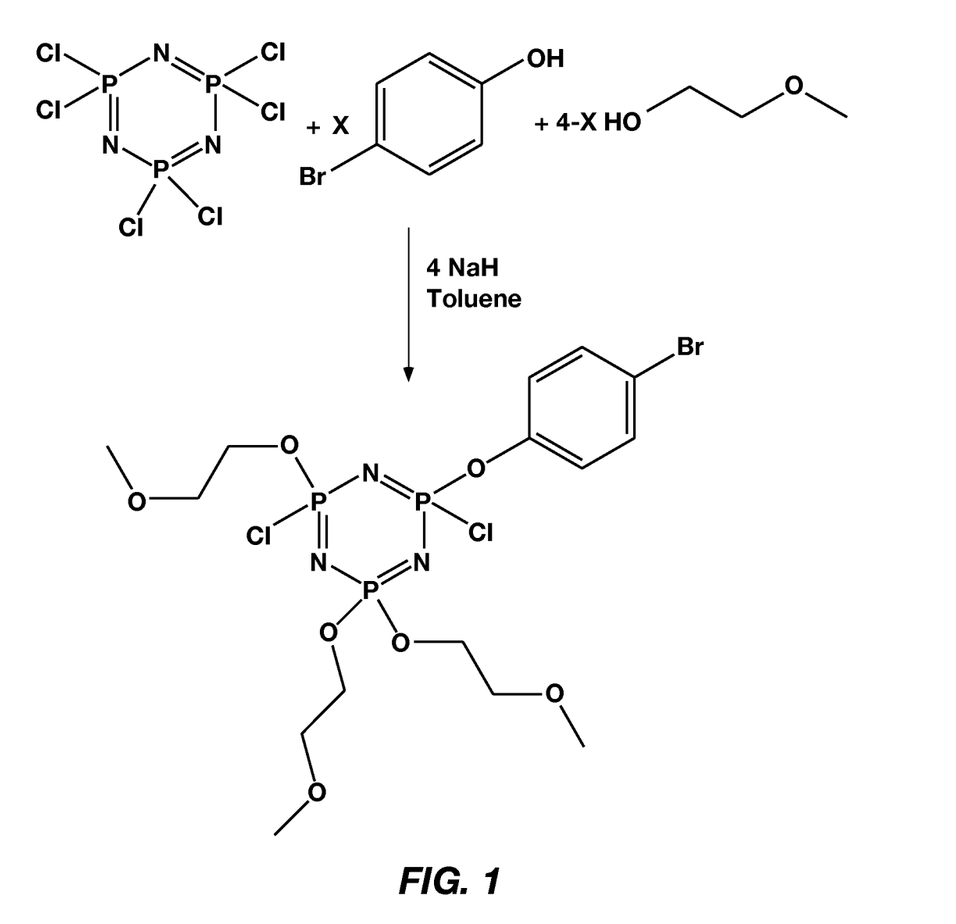
FIG. 1 illustrates an embodiment of producing an additive of the present disclosure.

By way of non-limiting example, to form the additive illustrated above, 4-bromophenol and 2-methoxyethanol may be reacted with the $N_3P_3Cl_6$, as shown in FIG. 1, where X is an integer of from 0 to 4. The products of the reaction include phosphazene compounds substituted with a combination of chlorine atoms, brominated phenoxy groups, and 2-methoxyethoxy groups, with the relative numbers of these groups dependent on the molar equivalents used of the reagents. While the additive shown in FIG. 1 is the predominant reaction product formed when one molar equivalent of 4-bromophenol (X=1), three molar equivalents of 2-methoxyethanol, and four molar equivalents of sodium hydride are reacted with the $N_3P_3Cl_6$ in tetrahydrofuran or other suitable aprotic solvent, other reaction products that differ in the relative numbers of chlorine atoms, brominated phenoxy groups, and/or 2-methoxyethoxy groups present on the additive may also be formed. The predominant reaction product may account for at least approximately 50% of the total reaction products, with the remainder of the reaction products including phosphazene compounds substituted with a statistical mixture of chlorine atoms, brominated phenoxy groups, and 2-methoxyethoxy groups based on the molar equivalents used of the reagents. The other reaction products may include phosphazene compounds having different combinations of chlorine atoms, brominated phenoxy groups, and 2-methoxyethoxy groups, such as more than or less than two chlorine atoms, more than one brominated phenoxy group, or more than or less than three 2-methoxyethoxy groups. Thus, the additive may include a statistical mixture of the first and second phosphazene compounds depending on the ratio of reagents used. Reaction products having a greater number of 2-methoxyethoxy groups relative to brominated phenoxy groups may have increased solubility in the resin formulation, while reaction products having a greater number of brominated phenoxy groups relative to 2-methoxyethoxy groups may have increased flame retardance.

To control the crosslink density of the wood product, a portion of the additive may include the second phosphazene compound, which has one reactive functional group, such as one chlorine atom. An example of such a phosphazene compound (where n=3) is shown below:

The one reactive functional group on the second phosphazene compound may react with the resin or with other phosphazene compounds of the additive, rather than with the wood product. Since this phosphazene compound has a single reactive site, the ability of the second phosphazene compound to propagate as a linear chain is limited, which reduces the crosslink density of the wood product. In contrast, a phosphazene compound having at least two reactive functional groups may bond more densely with the wood product, producing a higher degree of crosslink density. However, if the crosslink density of the wood product is too high, mechanical properties of the wood product may be affected, such as the wood product becoming brittle. Since the additive includes a statistical mixture of phosphazene compounds, a portion of the phosphazene compounds of the additive (those with two or more reactive functional groups) may react with the resin and the wood product, while another portion of the phosphazene compounds of the additive (those with only one reactive functional group) has a single reactive site and functions as a cap. By producing the additive to include the first and second phosphazene compounds, the desired mechanical properties of the wood product may be achieved when the additive is impregnated into the wood product.

Figure 2:
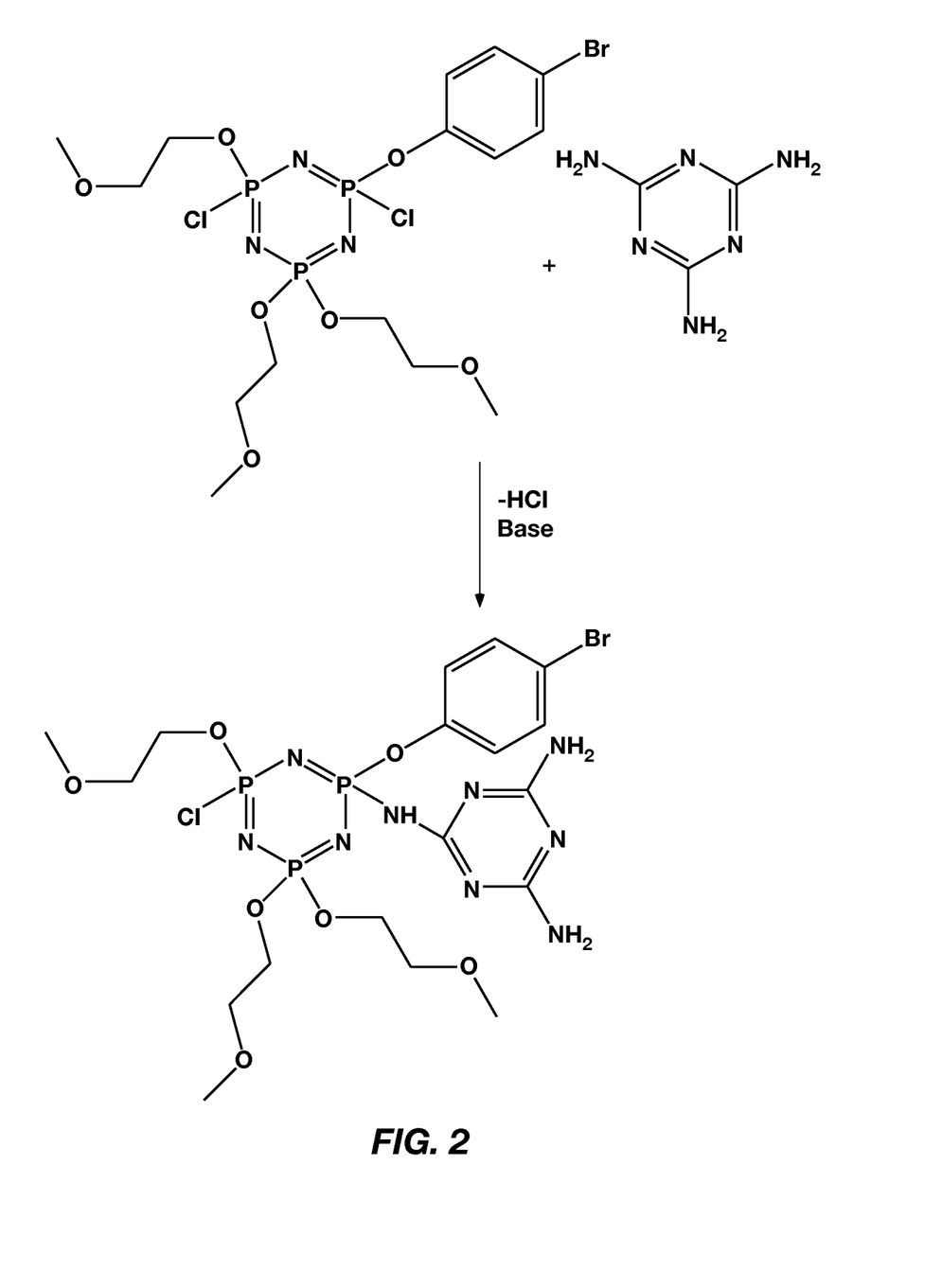
FIG. 2 illustrates an embodiment of reacting the additive with a melamine resin to produce an additive-resin reaction product of the present disclosure.
Figure 3:
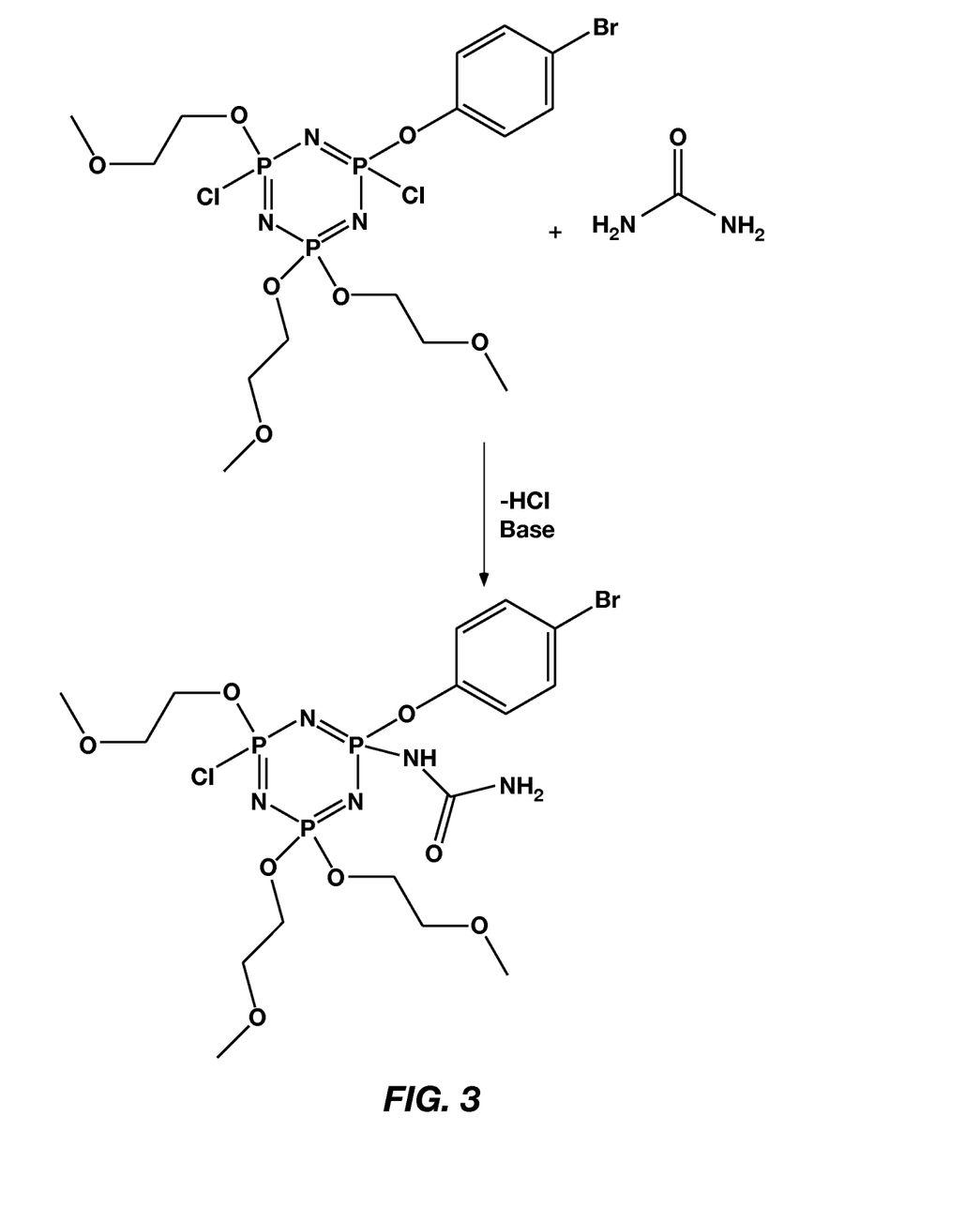
FIG. 3 illustrates an embodiment of reacting the additive with a urea resin to produce an additive-resin reaction product of the present disclosure.
Figure 4:
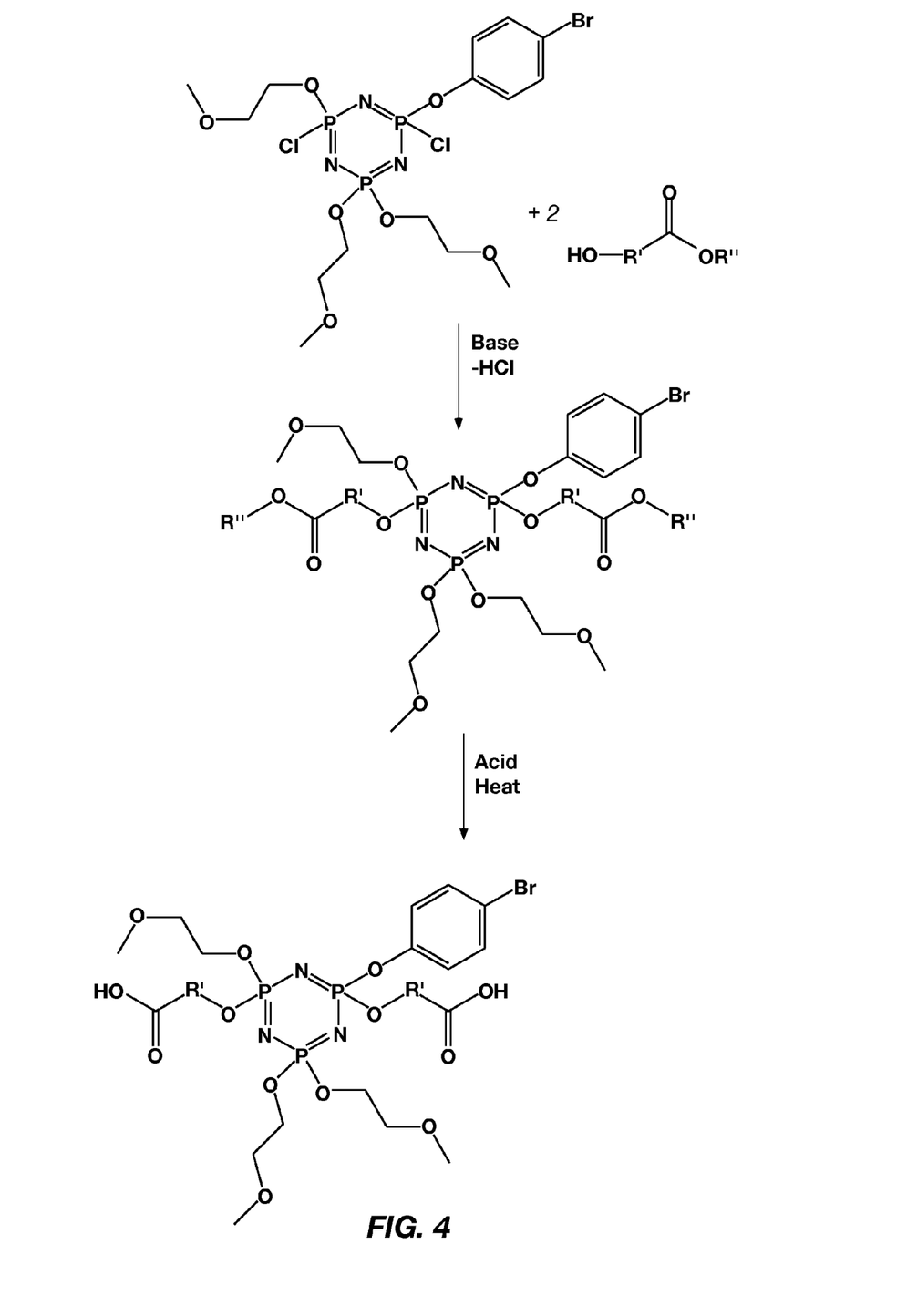
FIG. 4 illustrates an embodiment of reacting the additive with a polycarboxylic acid resin to produce an additive-resin reaction product of the present disclosure.
Figure 5:
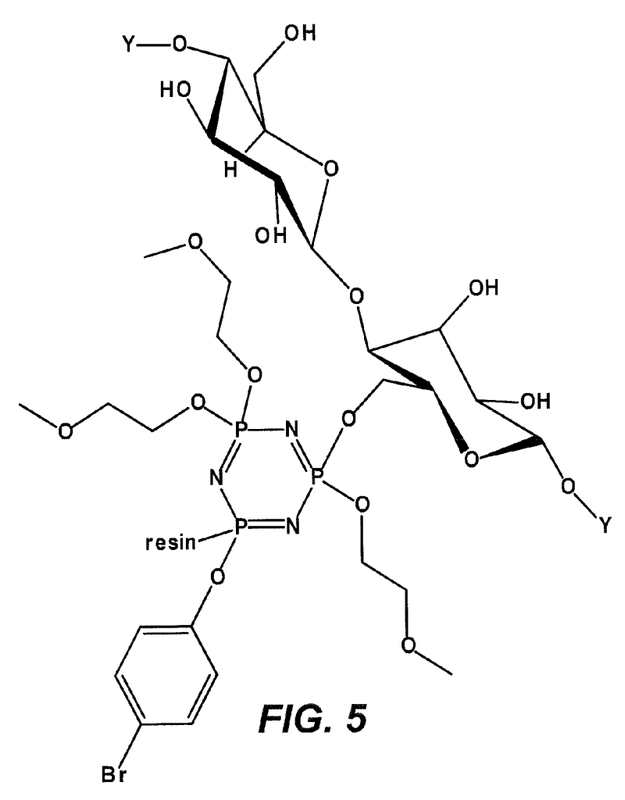
FIG. 5 illustrates an embodiment of an impregnated wood product of the present disclosure.

To incorporate the additive into the wood product, the additive may be reacted with the resin of the resin formulation, as shown in FIGS. 2-4, and with cellulose of the wood product, as shown in FIG. 5. While FIGS. 2-5 show the additive first reacting with the resin and then reacting with the cellulose, the additive may first react with the cellulose and then with the resin, or may react with the resin and cellulose substantially simultaneously. Until impregnation of the additive into the wood product is desired, the additive and the resin formulation may be maintained separately, such that the additive and the resin do not react. For convenience, the reaction product of the additive with the resin is referred to herein as the "additive-resin reaction product." The resin formulation may include an amine resin or a polycarboxylic acid (PCA) resin formulated into an aqueous-based solvent mixture. The amine resin may be produced by the reaction of an amine, such as melamine, urea, guanidine, benzoguanidine, or combinations thereof, with an aldehyde, such as formaldehyde, acetaldehyde, crotonaldehyde, benzaldehyde, or combinations thereof. By way of non-limiting example, the amine resin may be a melamine-formaldehyde (MF) resin, a urea- formaldehyde (UF) resin, a melamine-urea (MU) resin, or a melamine-urea-formaldehyde (MUF) resin. The aqueous-based solvent mixture may include water and at least one water-soluble or water-miscible organic solvent, such as methanol, ethanol, diethyl ether, acetone, or combinations thereof. The resin formulation may include from approximately 30 wt % to approximately 80 wt % water and from 20 wt % to 70 wt % of the amine resin or PCA resin. Amine resin formulations and PCA resin formulations are commercially available, such as from Georgia Pacific LLC (Atlanta, Ga.).

FIG. 2 shows a condensation reaction of the additive with melamine, while FIG. 3 shows a condensation reaction of the additive with urea. For the sake of simplicity, the resin is represented by a single monomer even though a second monomer, such as formaldehyde, may be present. One of the phosphorus-chlorine bonds of the additive may react with the amine groups on the resin, cross-linking the additive and the resin. The condensation reaction may proceed in the presence of a base. Since the amine groups of the resin may function as the base and since an excess of amine groups are present, the condensation reaction may be autocatalytic. The additive-resin reaction product may be dissolved, suspended, or emulsified in the aqueous-based solvent mixture of the resin formulation. Since the additive and resin are bonded to one another by reacting one of the reactive functional groups with a functional group on the resin, the remaining reactive functional group present on the additive-resin reaction product may either react with another molecule of resin or with the wood.

Since the additive may include a statistical mixture of different phosphazene compounds, as explained above, the additive-resin reaction product may include different phosphazene compounds, each of which is bonded to functional groups on the resin. The additive-resin reaction product may also include phosphazene compounds bonded to different molecules of the phosphazene compounds. Alternatively, the mixture of different phosphazene compounds may be purified by conventional techniques, which are not described in detail herein, to isolate a desired phosphazene compound, which is reacted with the resin to form a single additive-resin reaction product.

The remaining phosphorus-chlorine bond of the additive-resin reaction product may then react with hydroxyl groups present in the cellulose of the wood, cross-linking the additive-resin reaction product to the wood. For convenience, the reaction product of the additive-resin reaction product and the wood product is referred to herein as the "impregnated wood product." FIG. 5 shows a condensation reaction between the additive-resin reaction product, such as one of those illustrated in FIGS. 2-4, with cellulose to form the impregnated wood product. As known in the art, cellulose is a polymer of D-glucose. Two glucose units of cellulose are shown in FIG. 5, with "Y" designating additional glucose units. For simplicity, the resin portion of the additive-resin reaction product is indicated as "resin" in FIG. 5. While FIG. 5 shows the reaction of the additive-resin reaction product with a primary alcohol of cellulose, the additive-resin reaction product may also react with secondary alcohols present in cellulose. However, due to steric considerations, reaction of the additive-resin reaction product with primary alcohols of cellulose is more favored. Therefore, while the impregnated wood product shown in FIG. 5 is the predominant impregnated wood product produced by the condensation reaction, other products may be formed. The condensation reaction may proceed in the presence of a base and may be autocatalytic, as described previously, for the reaction of the additive and resin.

Figure 6:
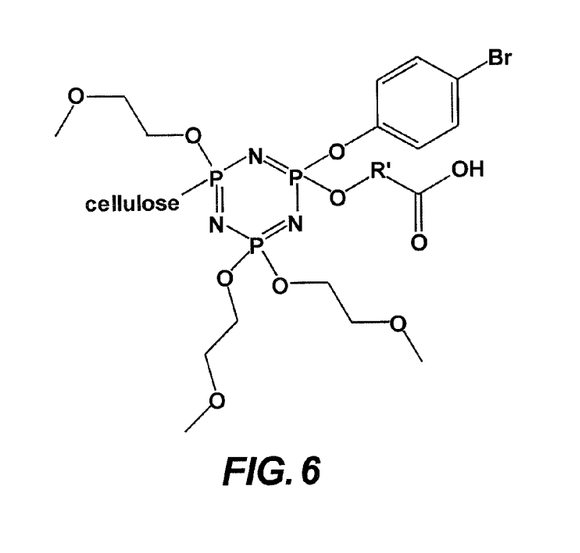
FIG. 6 illustrates an embodiment of an impregnated wood product of the present disclosure.

The additive may also be reacted with a PCA resin, as shown in FIG. 4, to form the additive-resin reaction product. The PCA resin may include a hydroxycarboxylic acid having the structure shown below:

where R' and R" are alkylene or alkyl groups, such as methylene or methyl, ethylene or ethyl, propylene or propyl, butylene or butyl, pentylene or pentyl, hexylene or hexyl, heptylene or heptyl, or octylene or octyl groups. Each of R' and R" may be independently selected. The hydroxycarboxylic acid may include, but is not limited to, aldaric acid, oxalic acid, malonic acid, malic acid, fumaric acid, succinic acid, glutaric acid, adipic acid, citric acid, isocitric acid, aconitic acid, propane-1,2,3-tricarboxylic acid, or 1,2,3,4-butanetetracarboxylic acid. The phosphorus-chlorine bonds of the additive may react with polycarboxylic acid groups of the PCA resin such that both chlorine atoms are replaced with esteric groups. The resulting esteric compound may be subjected to heat and acid to reduce the esteric groups to carboxylic acid groups, as shown in FIG. 4. One of the polycarboxylic acid groups may then react with the hydroxyl groups present in the cellulose of the wood, cross-linking the additive-resin reaction product to the wood, as shown in FIG. 6. For simplicity, the cellulose portion of the impregnated wood product has been labeled "cellulose" in FIG. 6. As described previously, the additive-resin reaction product may react with primary alcohol groups or secondary alcohol groups present in the cellulose. Alternatively, the additive may react with polycarboxylic acid groups such that only one chlorine atom is replaced with a polycarboxylic acid group (not shown). The remaining phosphorus-chlorine bond may then react with the hydroxyl groups present in the cellulose of the wood, cross-linking the additive-resin reaction product to the wood (not shown).

When impregnation of the additive into the wood product is desired, the wood product may be placed in a pressure vessel and the resin formulation added to the pressure vessel. The pressure vessel may be an autoclave or an oven configured to produce at least one of heat, a vacuum, and pressure. The additive may be admixed with the resin formulation, forming an additive-resin admixture. From approximately 1% by weight to approximately 10% by weight of the additive may be admixed with the resin. The additive-resin admixture may be applied to the wood product by conventional techniques including, but not limited to, brushing, spray coating, dip coating, immersion, soaking, or steeping. As such, the wood product may be exposed to the additive-resin admixture. The additive-resin admixture may be used to treat the wood product as soon as the additive-resin admixture is prepared. A delay in the immediate use of the additive-resin admixture is undesirable as the resin and the additive may begin to react with one another, which increases the molecular size of the additive and inhibits uniform penetration of the additive into the wood product, lessening the effectiveness of treating the wood product. The pressure vessel may be sealed and a vacuum or pressure produced in the pressure vessel to impregnate the additive-resin admixture into the wood product. The pressure vessel may be sealed at a temperature of from approximately 20° C. to approximately 100° C. and placed into a static vacuum for from approximately one minute to approximately ninety minutes. The pressure vessel may then be pressurized to a pressure $P_g$ of from approximately 100 psig to approximately 300 psig and left at ambient temperature for from approximately one hour to approximately five hours, enabling the additive and resin to penetrate into the wood product and react with cellulose of the wood product. Since the additive has a small molecular size, the additive may easily penetrate between fibers of the wood product. After depressurizing the pressure vessel, the wood product may be transferred to an oven or kiln to dry. The wood product may be heated to remove liquid components of the resin formulation and to further react the additive with the resin and cellulose of the wood product, forming the impregnated wood product. The heat may increase the rate of the condensation reaction between the additive-resin admixture and the cellulose. Heating the impregnated wood product also cures the wood, causing the additive and resin to remain in the wood fibers. Alternatively, or in addition, the wood product may be cured with microwave radiation to react the additive-resin admixture with the cellulose of the wood product.

By impregnating the additive-resin admixture into the wood product, the additive may bind to the wood fibers in the interior of the wood product, filling hollow fibers in the wood and forming a three-dimensional network of the phosphazene compound and resin within the wood product. The amount of additive impregnated into the wood product may be determined by comparing the weight of the wood product before impregnation and after drying of the impregnated wood product. The impregnated wood product may include from 0% to 120% of the additive-resin admixture, which has from approximately 1% by weight to approximately 10% by weight of the additive. The three-dimensional network provides additional density, hardness and mechanical strength to the wood product. Simultaneously, the presence of the additive in the impregnated wood product also reduces the flammability of the impregnated wood product compared to the flammability of an untreated wood product. The additive functions as an integral cross-linking component in the resin and contributes to increasing the strength and, therefore, the useful lifetime of the wood product. The additive also provides increased hydrophobicity and water resistance to the impregnated wood product. The impregnated wood product may visually appear to be similar to an untreated wood product except that the impregnated wood product may be heavier, harder, and more durable.

A wood product (Radiata pine) impregnated with the additive-resin admixture (a melamine-based resin having the additive) was subjected to a Steiner tunnel test to determine the flame spread and smoke density of the treated wood product. The treated wood product achieved a class A rating in the Steiner tunnel test.

While the disclosure may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the scope of the invention as defined by the following appended claims and their legal equivalents.

What is claimed is:

1. An additive, comprising:
at least two reactive functional groups and at least two capping functional groups bonded to phosphorus atoms of a first phosphazene compound, wherein one of the at least two reactive functional groups is configured to react with cellulose and the other of the at least two reactive functional groups is configured to react with a resin, and wherein one of the at least two capping functional groups is selected from the group consisting of a short chain ether group comprising a —OCH$_2$CH$_2$OR group where R is a methyl, ethyl, propyl, or butyl group, an alkoxy group comprising a —OR group where R is a methyl, ethyl, propyl, or butyl group, an amine group, and a thioether group, and the other of the at least two capping functional groups comprises an aryloxy group.

2. The additive of claim 1, wherein each of the at least two capping functional groups comprises a heteroatom through which each of the at least two capping functional groups is bonded to the phosphorus atoms of the first phosphazene compound.

3. The additive of claim 2, wherein the heteroatom is selected from the group consisting of oxygen, sulfur, selenium, and tellurium.

4. The additive of claim 2, wherein the at least two capping functional groups are not bonded to the phosphorus atoms of the first phosphazene compound by a nitrogen atom.

5. The additive of claim 1, wherein the first phosphazene compound comprises two reactive functional groups and four capping functional groups.

6. The additive of claim 1, wherein the at least two reactive functional groups comprise halogen atoms and each of the at least two capping functional groups is selected from the group consisting of a methoxyethoxy group and a brominated phenoxy group.

7. The additive of claim 1, wherein the additive has the following structure:

8. The additive of claim 1, further comprising a second phosphazene compound, the second phosphazene compound comprising one reactive functional group and at least one capping functional group.

* * * * *